US008062899B1

(12) United States Patent
Oguri

(10) Patent No.: US 8,062,899 B1
(45) Date of Patent: Nov. 22, 2011

(54) IDENTIFICATION AND QUANTITATIVE DETERMINATION OF MAJOR CHEMICAL CONTAMINANTS ASSOCIATED WITH L-TRYPTOPHAN

(75) Inventor: Elisha R. Oguri, Santa Fe Springs, CA (US)

(73) Assignee: NHK Laboratories, Inc., Santa Fe Springs, CA (US)

( * ) Notice: Subject to any disclaimer, the term of this patent is extended or adjusted under 35 U.S.C. 154(b) by 0 days.

(21) Appl. No.: 12/347,892

(22) Filed: Dec. 31, 2008

Related U.S. Application Data

(60) Provisional application No. 61/018,356, filed on Dec. 31, 2007.

(51) Int. Cl.
*G01N 30/02* (2006.01)
*G01N 21/00* (2006.01)

(52) U.S. Cl. ..... 436/161; 436/527; 436/805; 422/82.05; 422/82.09

(58) Field of Classification Search ............ 436/161; 73/61.52, 61.55, 61.59, 61.71, 61.72; 530/417
See application file for complete search history.

(56) References Cited

U.S. PATENT DOCUMENTS 5,993,653 A * 11/1999 Ahmed et al. ............. 210/198.2

OTHER PUBLICATIONS

Phenomenex Gemini Two-In-One-Technology (Twin Technology), 2004.*
Zhao et al., 1999, Carcinogenesis, vol. 20, No. 11, pp. 2101-2108.*
Hill, Robert H., Jr. et al., "Contaminants in L-Tryptophan Associated with Eosinophelia Myalgia Syndrome," Arch. Environ. Contam. Toxicol. 25, 134-142 (1993).
Williamson, B.L., et al., "On-line HPLC-tandem mass spectrometry analysis of contaminants of L-tryptophan associated with the onset of eosinophelia-myalgia syndrome," Toxicology Letters, 92(2), 139-148 (1997)—Abstract only.
ESA Note 5600A, "Tryptophan Contamination," ESA, Inc.
Trucksess, MW, et al., "High-performance liquid chromatographic determination of 1,1'-ethylidenebis(L-tryptophan) in L-tryptophan preparations," J. Pharm. Sci., 83(5), 720-722 (May 1994)—Abstract only.
Zangrilli, JG, et al., "1,1'-Ethylidenebis[L-tryptophan], an impurity in L-tryptophan associated with eosinophelia-myalgia syndrome, stimulates type I collagen gene expression in human fibroblasts in vitro," Biochem. Mol. Biol. Int., 37(5), 925-933 (Nov. 1995)—Abstract only.
Trucksess, MW, "Separation and isolation of trace impurities in L-tryptophan by high-performance liquid chromatography," J. Chromatogr., 630(1-2), 147-150 (Feb. 5, 1993)—Abstract only.
Smith, M.J., et al., "1,1'-Ethylidenebis(l-tryptophan), Structure Determination of Contaminant "97"—Implicated in the Eosinophelia-Myalgia Syndrome (EMS)," Tetrahedron Letters, 32(8), 991-994 (1991).
Love, L. A., et al., "Pathological and Immunological Effects of Ingesting L-Tryptophan and 1,1'-Ethylidenebis(L-Tryptophan) in Lewis Rats," J. Clinical Invest., 91, 804-811 (Mar. 1993).

* cited by examiner

*Primary Examiner* — Krishnan S Menon
*Assistant Examiner* — Allison M Gionta
(74) *Attorney, Agent, or Firm* — Amin Tatati, LLC; Janine A. Moderson; George M. Carrera, Jr.

(57) ABSTRACT

An improved chromatographic method for the separation, identification and quantification of contaminants associated with Eosinophelia-Myalgia Syndrome (EMS) includes a high pressure liquid chromatography (HPLC) method which utilizes a silica-based column and a gradient mobile phase. The method provides for effective, efficient, and economical quantitative and qualitative identification of 1,1'-Ethylidenebis L-tryptophan (EBT), 2,3-indolymethyl L-tryptophan (Peak 200), and 2-anilino-L-alanine (Peak 1).

15 Claims, No Drawings

IDENTIFICATION AND QUANTITATIVE DETERMINATION OF MAJOR CHEMICAL CONTAMINANTS ASSOCIATED WITH L-TRYPTOPHAN

This application claims the benefit of earlier filed Provisional U.S. Patent Application Ser. No. 61/018,356 filed on Dec. 31, 2007.

FIELD OF THE INVENTION

The present invention generally relates to separation, identification and quantification of various contaminants associated with L-Tryptophan. More particularly, the present invention relates to methods for determining the purity of L-Tryptophan via the detection and quantification of contaminants associated with Eosinophelia-Myalgia Syndrome (EMS).

BACKGROUND OF THE INVENTION

L-Tryptophan is an important amino acid that is marketed across America as a dietary supplement in the form of tablets, capsules, and powders. Although L-Tryptophan is legally defined as a dietary supplement by the Dietary Supplement Health and Education Act of 1994 (DSHEA), L-Tryptophan is primarily sold in the U.S. as a prescription drug. As a drug, L-Tryptophan is used to treat restlessness, insomnia, depression, and premenstrual syndrome (PMS) among other conditions. L-Tryptophan received widespread international attention in 1989 when tainted batches of L-Tryptophan dietary supplements caused Eosinophelia-Myalgia Syndrome (EMS) in a large number of people, ultimately leading to death in some cases.

Medical professionals related the syndrome to consumption of L-Tryptophan that was manufactured by using a bacterial fermentation process by Showa Denko K. K., Japan. Further investigation into the tainted batches revealed the contaminant to be trace chemicals identified as peak "X" on the monograph. The source of the contaminants was reported to have originated from specific strains of the bacterium Bacillus amyloliquefaciens used in the production process. Approximately 60 trace contaminants were identified in the tainted L-Tryptophan associated with the EMS outbreak. However, three compounds, namely, EBT (1,1'-Ethylidenebis L-tryptophan), Peak 200 (2,3-indolymethyl L-tryptophan), and Peak 1 (3-anilino-L-alanine) are considered as EMS-causing contaminants. All three of these compounds are collectively referred to as peak "X."

L-Tryptophan continues to be commercially manufactured using bacterial fermentation; a process which may inadvertently result in trace chemical compounds, which are components of the collective EMS contaminant. Although effective purification methods are in place to separate and remove contaminants, the presence of potential EMS causing contaminants is not comprehensively documented or standardized.

In view of the above, there is a need and a demand for a standard method for the separation, identification, and quantification of contaminants in L-Tryptophan associated with EMS.

There is further need and demand for a method for the separation, identification, and quantification of EMS-associated contaminants in L-Tryptophan that is economical and/or straightforward to implement in a manufacturing setting.

SUMMARY OF THE INVENTION

A general object of the invention is to provide an analytical method designed to quantitatively and qualitatively identify the presence of potential EMS-causing contaminants.

A more specific object is to overcome one or more of the problems described above.

The general object of the invention can be obtained, at least in part, through a quantitative and qualitative analytical methodology utilizing high pressure liquid chromatography (HPLC) designed to separate, identify, and quantify potential EMS causing contaminants in L-Tryptophan preparations. The methods are designed to aid L-Tryptophan manufacturers by standardizing the analytical method for identifying potential contaminants in L-Tryptophan batches which inexorably can exist due to the nature of the commercial manufacturing process.

The method utilizes an HPLC system which includes several components including a system controller, a liquid sample injector, liquid chromatographic pumps, liquid degassers, and a detector. The HPLC column used to separate the contaminant components is an economical C-18 column.

A sample of L-Tryptophan is dissolved in a solution which is injected into the HPLC system by the liquid sample injector, suitably an autoinjector. Individual chemical contaminants in the sample solution are separated by a column and eluted at specific time after injection and detected by an ultraviolet (UV) detector. A chromatographic profile of eluted components is integrated and generated by the system controller. Each chemical contaminant is eluted over a specific time interval and is depicted as a peak in the chromatogram. The area under each peak of the chromatogram is quantitatively measured to determine the amount of the contaminant present in the L-Tryptophan sample.

Other objects and advantages will be apparent to those skilled in the art from the following detailed description taken in conjunction with the drawings and examples.

DETAILED DESCRIPTION

The present invention relates to an improved method for detecting and quantifying Eosinophelia-myalgia syndrome-associated contaminants in L-Tryptophan preparations. The concept of the present invention relies on an economical and efficient analytical method which employs a high-performance liquid chromatography (HPLC) system equipped with a chromatographic column that is robust and relatively immune or resistant to fouling by other chemicals and contaminants. The EMS-associated contaminants are injected into the column and sequentially eluted using a liquid mobile phase suitable for effectively and efficiently separating individual components of the L-Tryptophan sample, thereby allowing for detection and quantification of the compounds of interest.

Eosinophelia-myalgia syndrome (EMS) has been linked to ingestion of contaminants in L-Tryptophan preparations. Of particular interest are three compounds, namely, EBT (1,1'-Ethylidenebis tryptophan), Peak 200 (2,3 indolymethyl L-tryptophan), and Peak 1 (3-anilino-L-alanine) considered to be the primary EMS-causing contaminants. Prior methods for detecting and/or quantifying contaminants in L-Tryptophan preparations have not been as effective or as efficient as desired in that they typically have required the use of expensive chromatographic columns, employed complicated mobile phases and/or elution gradients, and/or have result in incomplete separation of the contaminants of interest.

In an effort to overcome the above obstacles and/or complications it has been discovered that EBT, Peak 200, and Peak 1 can be effectively, efficiently, and economically separated, identified, and quantified by utilizing a reverse-phase HPLC system equipped with a chromatographic column containing a robust C18 stationary phase having a 5 micrometer (μm) spherical particle size with a 110 angstrom (Å) pore size. The C18 stationary phase suitably includes a silica-organic layer grafted to an underlying silica matrix such that the C18 stationary phase has a carbon load of approximately 14%. The C18 stationary phase is advantageously robust in that it has extended pH stability (i.e., over a pH range of about 1 to about 12) and is substantially (i.e., about 100%) stable in aqueous environments. In accordance with certain embodiments, the C18 chromatographic column has a length of about 15 centimeters (cm) and an inner diameter of about 4.6 millimeters (mm). One simple, less expensive, stable, and rugged C18 chromatographic column is available under the trade name Gemini C18 from Phenomonex, Inc. of Torrance, Calif.

The chromatographic column is incorporated with a HPLC system including a system controller, an auto sample injector, liquid chromatograph pumps, a liquid degasser, and an ultraviolet (UV) detector. Suitably, the UV detector is set to a wavelength of about 223 nanometers (nm) to achieve maximum signal strength. One suitable system is available from Shimadzu Scientific Instruments, Inc. of Columbia, Md. and includes an SCL 10Avp system controller, an SIL 10ADvp auto sample injector, at least two LC 10 ATvp liquid chromatographic pumps, a DGU 14A liquid degasser for removing entrapped gases from the mobile phases(s), and a SPD 10Avp UV detector set at a wavelength of 223 nm.

The method for separating, identifying, and quantifying EMS-associated contaminants of L-Tryptophan employs a linear gradient mobile phase including or consisting of two parts: (1) Mobile Phase A (MPA) including or consisting of about 10% by volume acetonitrile and about 90% by volume water with about 0.1% trifluoroacetic acid; and (2) Mobile Phase B (MPB) including or consisting of about 50% by volume acetonitrile and about 50% by volume water with about 0.1% trifluoroacetic acid.

In accordance with certain embodiments, the system controller is programmed to deliver a gradient mobile phase at a rate of about 1 milliliter (ml) per minute from the beginning of a sample run at a ratio of MPA to MPB of:

100% MPA for 10 minutes from injection of an L-Tryptophan sample;

a first linear gradient that goes from 100% MPA to a ratio of 90% MPA to 10% MPB at about 20 minutes from injection;

a second linear gradient that goes from a ratio of 90:10 MPA/MPB to 100% MPB at about 55 minutes from injection; and 100% MPA at 55.1 minutes from injection to the end of the sample run. The solvent strengths and gradient flow demonstrated effective and efficient resolution of peaks in the chromatogram corresponding to the EMS-associated compounds EBT, Peak 200, and Peak I.

L-Tryptophan samples for analysis can be prepared by dissolving or dispersing about 100 milligrams (mg) of an L-Tryptophan preparation in about 10 ml of a solution including or consisting of about 50% by volume methanol and about 50% by volume water. The L-Tryptophan samples are subsequently centrifuged and a supernatant fluid is collected in a glass vial or other suitable container. Portions of the supernatant fluid can be further filtered through a suitable media such as, for example, a cellulose fiber filter paper having a pore size of about 20-25 μm. One suitable cellulose fiber filter paper includes a standard grade 4 paper available from Whatman, Inc. of Florham Park, N.J.

According to certain embodiments, an aliquot of about 100 μl of the L-Tryptophan sample is injected into the above-described system for the separation, identification, and quantification of the EMS-associated contaminants EBT, Peak 200, and Peak 1.

EXAMPLE

A sample solution of an L-Tryptophan preparation associated with an EMS outbreak was prepared by according to the above described method. A 100 μl aliquot of the sample solution was injected into a Shimadzu HPLC system, as described above, including a Phenomenex® Gemini 5 μm C18 column having a length of 15 cm and an inner diameter of 4.6 mm. The sample run was conducted according to the above μl described mobile phase gradient program. The UV detector was set to a wavelength of about 223 nm. The EMS-associated contaminants EBT and Peak 200 eluted at about 30 minutes and 36 minutes, respectively.

While particular elements, embodiments, and applications of the present invention have been shown and described, it is understood that the invention is not limited thereto because modifications may be made by those skilled in the art, particularly in light of the foregoing teaching. It is therefore contemplated by the appended claims to cover such modifications and incorporate those features which come within the spirit and scope of the invention.

I claim:

1. A method for separating, detecting and quantifying contaminants associated with L-Tryptophan induced eosinophelia-myalgia syndrome (EMS), comprising:

preparing an L-Tryptophan sample;

injecting the L-Tryptophan sample into a high performance liquid chromatographic (HPLC) system equipped with a column including a C18 silica-based stationary phase, wherein the C18 silica-based stationary phase comprises spherical particles;

separating and eluting the EMS-associated contaminants using a gradient mobile phase program including the steps of:

delivering 100% Mobile Phase A (MPA) for 10 minutes from injection of the L-Tryptophan sample;

running a first linear gradient that goes from 100% MPA to a ratio of 90% MPA to 10% Mobile Phase B (MPB) at about 20 minutes from injection;

running a second linear gradient that goes from a ratio of 90:10 MPA/MPB to 100% MPB at about 55 minutes from injection;

detecting a presence of an EMS-associated contaminant using a UV detector set to a wavelength of about 223 nm; and quantifying at least one EMS-associated contaminant selected from the group consisting of 1,1'-Ethylidenebis L-tryptophan (EBT), 2,3-indolymethyl L-tryptophan (Peak 200), 3-anilino-L-alanine (Peak 1) and combinations thereof, wherein MPA includes about 10% acetonitrile in water with about 0.1% trifluoroacetic acid (TFA) and MPB includes about 50% acetonitrile in water with about 0.1% TFA.

2. The method according to claim 1, wherein the L-Tryptophan sample is prepared by dissolving an L-Tryptophan preparation in a methanol/water solution.

3. The method according to claim 2, wherein the L-Tryptophan preparation is dissolved in a solution having a ratio of methanol to water of between about 15:85 and about 50:50 by volume.

4. The method according to claim 1, wherein about 100 microliters (μl) of the L-Tryptophan sample is injected into the HPLC system.

5. The method according to claim 1, wherein said spherical particles have a particle size of about 5 micrometers (μm) and the stationary phase particles include a silica-organic layer grafted to a silica support.

6. The method according to claim 1, wherein the chromatographic column has a length of about 15 centimeters (cm) and an inner diameter of about 4.6 millimeters (mm).

7. The method according to claim 1, further comprising:
delivering a gradient mobile phase at a rate of about 1 milliliter (ml) per minute, wherein the gradient mobile phase comprises Mobile Phase A (MPA) and Mobile Phase B (MPB).

8. The method according to claim 1, further comprising:
quantifying an amount of EMS-associated contaminants via analysis of a chromatogram generated by the HPLC system,
wherein an area under a peak corresponding to an EMS-associated contaminant is compared to a standard peak area to determine the amount of an EMS-associated contaminant present in the L-Tryptophan sample.

9. A method for detecting eosinophelia-myalgia syndrome (EMS) associated contaminants in a sample, the method comprising the steps of:
(a) introducing said sample onto a C18 silica-based stationary phase of a high performance liquid chromatographic (HPLC) column,
wherein said C18 silica-based stationary phase comprises spherical particles with a grafted silica-organic layer upon a silica matrix, and
wherein said stationary phase is stable at a pH of about 12;
(b) delivering a gradient mobile phase at a rate sufficient to detect said contaminants,
wherein the gradient mobile phase comprises a first mobile phase, Mobile Phase A (MPA), and a second mobile phase, Mobile Phase B (MPB);
wherein MPA includes about 10% acetonitrile in water with about 0.1% trifluoroacetic acid (TFA) and MPB includes about 50% acetonitrile in water with about 0.1% TFA, and
wherein the gradient mobile phase is delivered according to a gradient mobile phase program including the steps of:
delivering 100% Mobile Phase A (MPA) for 10 minutes from injection of the L-Tryptophan sample;
running a first linear gradient that goes from 100% MPA to a ratio of 90% MPA to 10% Mobile Phase B (MPB) at about 20 minutes from injection;
running a second linear gradient that goes from a ratio of 90:10 MPA/MPB to 100% MPB at about 55 minutes from injection;
(c) detecting a presence of said EMS-associated contaminants using a UV detector set to a wavelength of about 223 nm; and
(d) quantifying at least one EMS-associated contaminants selected from the group consisting of 1,1'-Ethylidenebis L-tryptophan (EBT), 2,3-indolymethyl L-tryptophan (Peak 200), 3-anilino-L-alanine (Peak 1), and combinations thereof.

10. The method of claim 9, wherein said sample comprises L-Tryptophan.

11. The method of claim 10, wherein said introducing step (a) further comprises:
(a1) injecting said sample into said high performance liquid chromatographic (HPLC) column of an HPLC system.

12. The method of claim 9, wherein said spherical particles have a particle size of about 5 micrometers (μm).

13. The method of claim 9, wherein said delivering step (b) further comprises delivering the gradient mobile phase at a rate of about 1 milliliter (ml) per minute.

14. The method of claim 9, wherein said detecting step (c) further comprises the step of:
(c1) separating and eluting any of the EMS-associated contaminants.

15. The method of claim 9, wherein said spherical particles have a particle diameter of about 5 micrometer (μm), a pore size of 110 angstroms (Å), and a carbon load of about 14%; and
wherein said gradient profile further comprises running a third linear gradient to 100% MPA after about 55 minutes from injection.

* * * * *